(12) United States Patent
Ernst et al.

(10) Patent No.: US 6,610,892 B2
(45) Date of Patent: Aug. 26, 2003

(54) PROCESS FOR PREPARING 2,7-DIMETHYL-2,4,6-OCTATRIENAL MONOACETALS

(75) Inventors: Hansgeorg Ernst, Speyer (DE); Klaus Henrich, Hassloch (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/094,819

(22) Filed: Mar. 12, 2002

(65) Prior Publication Data
US 2002/0128519 A1 Sep. 12, 2002

(30) Foreign Application Priority Data
Mar. 12, 2001 (DE) .......................... 101 12 067

(51) Int. Cl.[7] .......................... C07C 45/29; C07C 45/41
(52) U.S. Cl. .......................... 568/460; 568/596; 568/600; 549/369; 549/374; 549/375; 549/376; 549/430; 549/454; 560/183; 560/186; 560/187
(58) Field of Search .......................... 549/369, 375, 549/374, 376, 454, 430; 560/183, 186, 187; 568/460, 596, 600

(56) References Cited

U.S. PATENT DOCUMENTS

| 4,543,417 A | 9/1985 | Schmieder et al. ......... 549/375 |
| 5,118,866 A | 6/1992 | Knaus et al. ............... 568/447 |

FOREIGN PATENT DOCUMENTS

| DE | 37 05 785 | 9/1988 | .......... C07C/175/00 |
| DE | 44 40 286 | 5/1996 | .......... C07C/403/14 |
| DE | 44 40 287 | 5/1996 | ............ C07C/69/73 |
| EP | 0 112 502 | 7/1984 | .......... C07C/69/732 |
| EP | 0 718 283 | 6/1996 | .......... C07C/403/14 |
| GB | 2 301 775 | 12/1996 | .......... A61K/31/07 |

OTHER PUBLICATIONS

Griffith et al. "Preparation and Use of Tetra–n–butylammonium Per–ruthenate (TBAP reagent) and Tetra–n–propylammonium Per–ruthenate (TPAP reagent) † as new catalytic oxidants" J. of Chemical Society Chemical Communications No. 21 (1987) pp. 1625–1627.

Muraki et al. "Aminoaluminum Hydride as new Reducing Agents. II Selective Reduction of Esters of Carboxylic Acids to Aldehydes" Chemistry Letters No. 1 (1975) pp. 215–218.

Helvetica Chimica Acta vol. 64 (1981) pp. 2463–2469 & 2469–2484.

Jansen et al. "Synthesis and characterization of all–E (12, 12'–$^{13}C_2$)–, (14,14'–$^{13}C_2$)–, (15,15'–$^{13}C_2$)–and (20,20'–$^{13}C_2$) astaxanthin" Recl. Trav. Chim. Pays–Bas 113 (1994) pp. 552–562.

(List continued on next page.)

Primary Examiner—Rosalynd Keys
(74) Attorney, Agent, or Firm—Keil & Weinkauf

(57) ABSTRACT

The invention relates to a process for preparing 2,7-dimethyl-2,4,6-octatrienal monoacetals of the general formula I

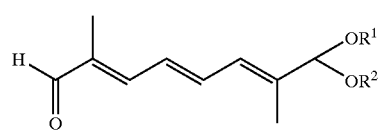

which comprises
a) condensing an ester phosphonium salt of the general formula II or an ester phosphonate of the general formula III

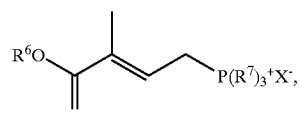

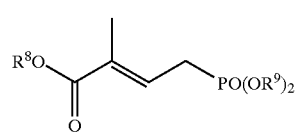

with an aldehyde of the formula IV

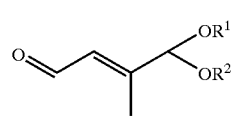

in a Wittig or Wittig-Horner reaction to give an acetal ester of the general formula V

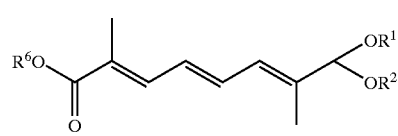

b) reducing the ester of the formula V to give an acetal alcohol of the general formula VI

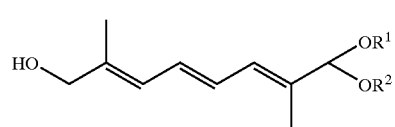

and
c) oxidizing the alcohol to 2,7-dimethyl-2,4,6-octatrienal monoacetals of the general formula I, where the substituents have the meaning defined in the description.

10 Claims, No Drawings

OTHER PUBLICATIONS

Jansen et al. "Synthesis of isotopically labelled cartenoids; investigations on structure and function of cartenoproteins at the atomic level" Pure & Appl. Chem. vol. 66, No. 5 (1994) pp. 963–972.

Bone et al. "Distribution of Lutein and Zeaxanthin Stereoisomers in the Human Retina" Exp. Eye Res. vol. 64 (1997) pp. 211–218.

Jansen et al. "Synthesis of Isotopically labelled carotenoid; investigations on structure and function of carotenoproteins at the atomic level" Pure & Applied Chem. vol. 66, No. 5 (1994) pp. 963–972.

Zumbrunn et al. "Synthesen von Caroteinen mit Ψ–Endgruppen und (Z)–Konfiguration and Terminalen Konjugierten Doppelbindungen" Helvetica Chimca Acta vol. 68 (1985) pp. 1519–1539.

PROCESS FOR PREPARING 2,7-DIMETHYL-2,4,6-OCTATRIENAL MONOACETALS

The invention relates to a novel process for preparing 2,7-dimethyl-2,4,6-octatrienal monoacetals (also referred to hereinafter as $C_{10}$-dialdehyde monoacetals) of the general formula I,

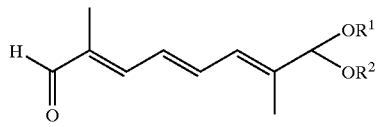

I in which the substituents $R^1$ and $R^2$ may, independently of one another, be $C_1$–$C_8$-alkyl or, together with the oxygen atoms and the carbon atoms to which they are bonded, form a 1,3-dioxolane or 1,3-dioxane ring of the following structures.

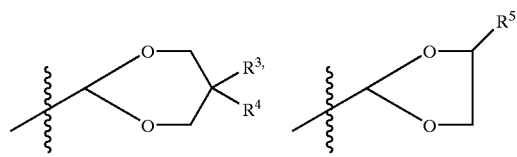

Monoacetals of this structure are required according to Helv. Chim. Acta 1981, 64 (7), 2469 for the selective synthesis of $C_{40}$-carotenoids with a nonsymmetrical structure.

Protection of one of the two carbonyl groups in the central $C_{10}$ building block (9) in the following reaction scheme makes it possible to carry out the Wittig reactions with the two $C_{15}$ phosphonium salts (2) and (5) very selectively in succession and thus obtain a carotenoid (6) which is free of the products (7) and (8) with symmetrical structures, whose formation is unavoidable on use of an unprotected $C_{10}$-dialdehyde (9).

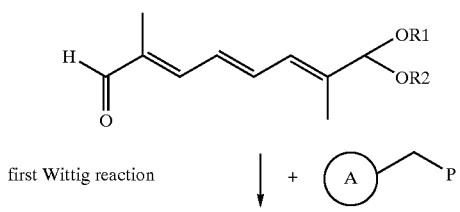

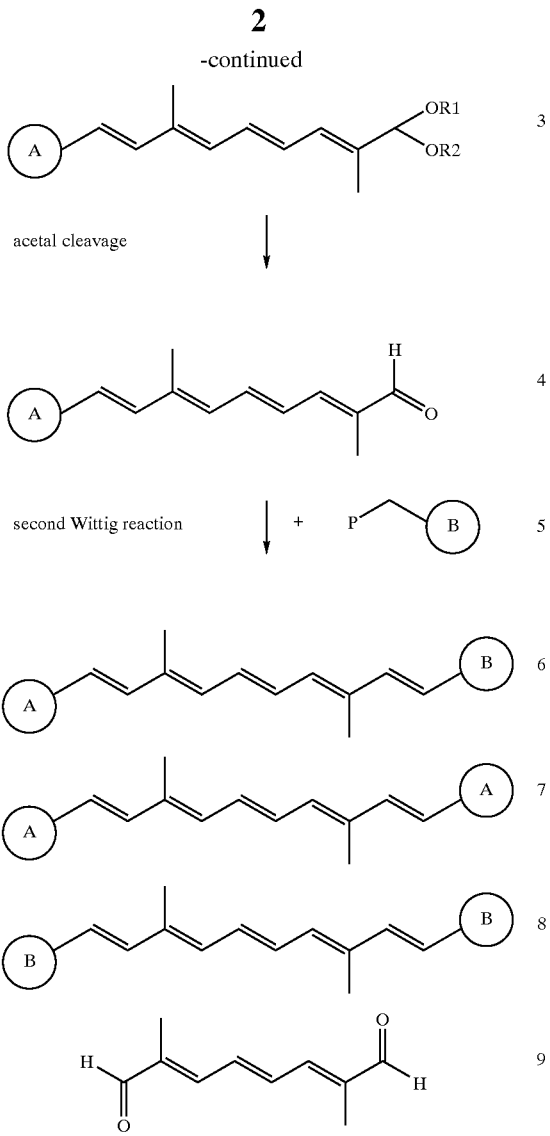

Of particular interest from the group of carotenoids which have a nonsymmetrical structure with different end groups A and B are lutein (10) and meso-zeaxanthin (11) because these carotenoids protect inter alia the human eye from blindness resulting from age-related macular degeneration [Exp. Eye Res. 1997, 64 (2), 211–218; GB 2301775 (1996)].

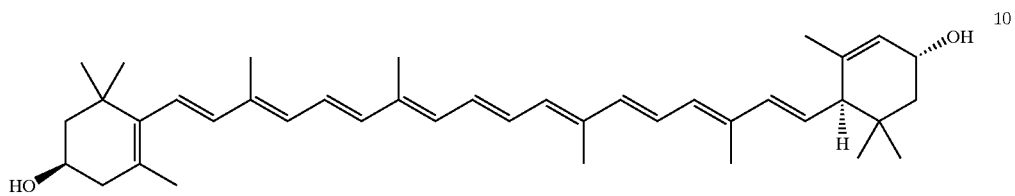

Lutein

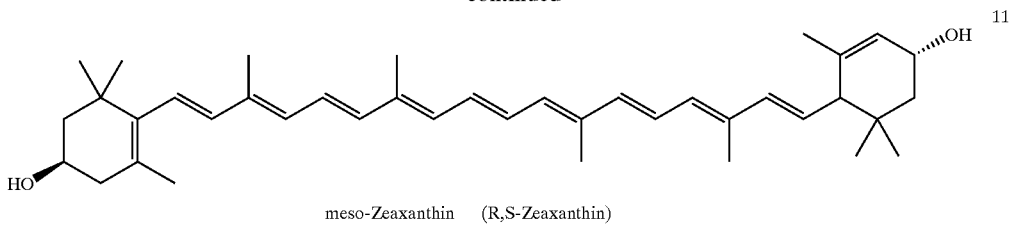

meso-Zeaxanthin (R,S-Zeaxanthin)

In order to obtain meso-zeaxanthin (11) which is free of R,R-zeaxanthin (12) and S,S-zeaxanthin (13) it is necessary, for example, for the two Wittig reactions of the central $C_{10}$ building block with the R—$C_{15}$ phosphonium salt (14) to give a $C_{25}$ intermediate (15), and its reaction with the S—$C_{15}$ phosphonium salt (16) to take place completely selectively in succession.

Thus, for example, the dimethyl acetal (17) can be obtained by p-toluenesulfonic acid-catalyzed acetalyzation of the dialdehyde (9) [Helv. Chim. Acta 1981, 64 (7), 2469]. The process includes a complicated low-temperature crystallization, and the product can be obtained only in inadequate yield.

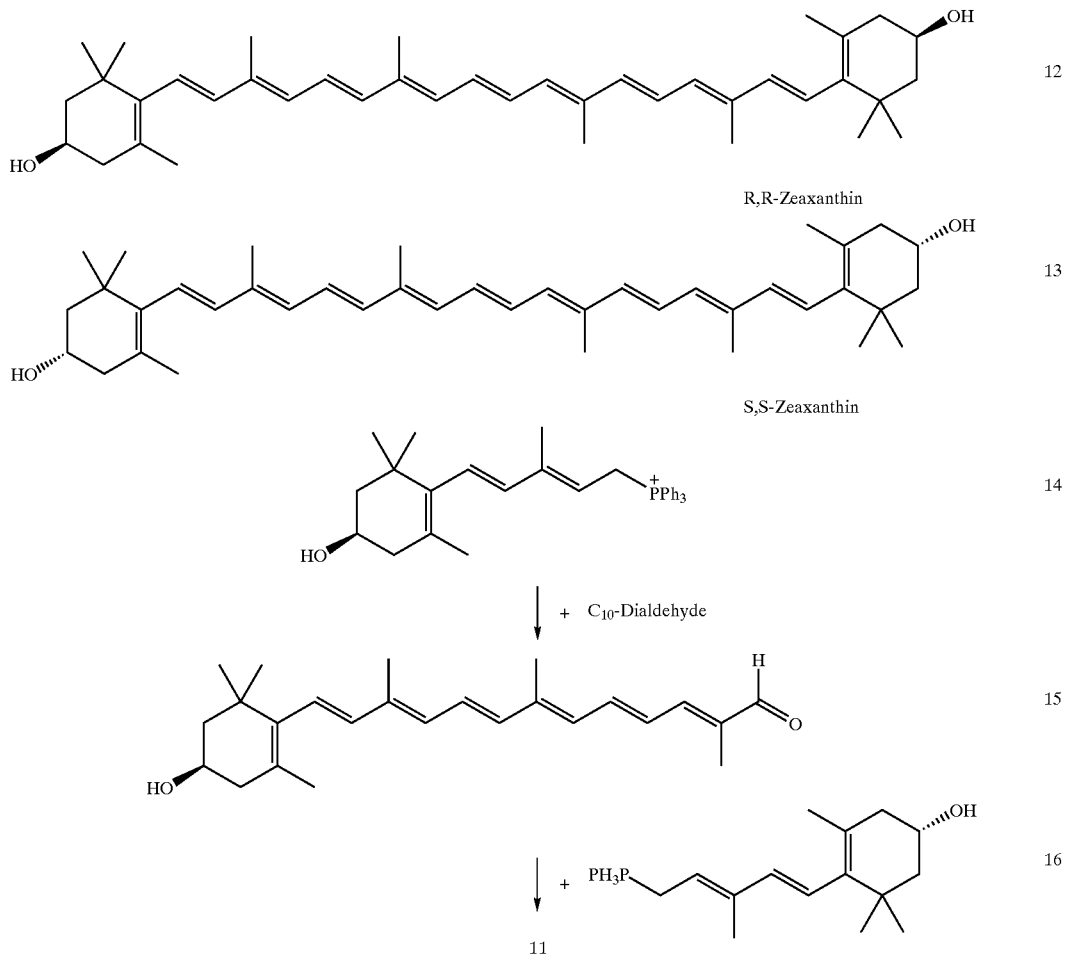

These requirements also apply analogously to the synthesis of lutein.

The selectivity of the two Wittig reactions which is necessary for synthesizing a pure product is ensured only if a $C_{10}$-dialdehyde in which one carbonyl group is in protected form as acetal is employed.

Various syntheses of $C_{10}$-dialdehyde monoacetals have been described in the literature:

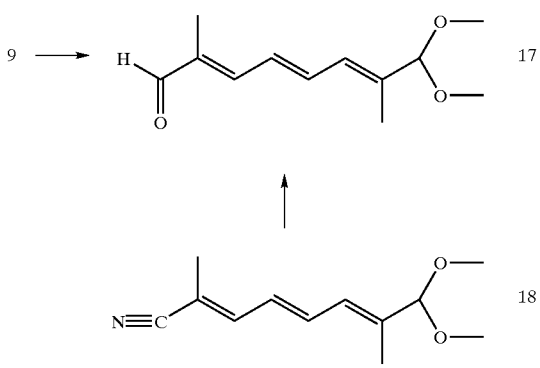

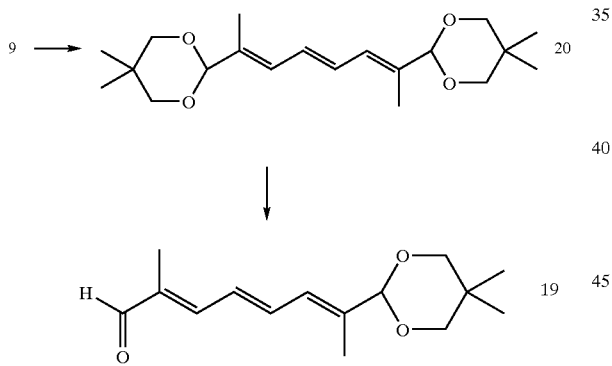

Another synthetic process relates to the formation of the aldehyde function by reduction of the corresponding nitrile (18) [Pure & Appl. Chem. 1994, 66 (5), 963; Recl. Trav. Chim. Pays-Bas 1994, 113, 552]. This reduction is effected with diisobutylaluminum hydride at −70° C. The complete synthesis, which is described only on the mmol scale, has the aim of introducing $^{13}C$ isotopes and has no industrial significance.

The synthesis described in the literature of the $C_{10}$-dialdehyde mononeopentyl glycolacetal (19) is based on the selective cleavage of the corresponding bisneopentyl glycolacetal (20) to the monoacetal by brief contact with HCl. This synthesis is likewise described only on the mmol scale. Because the selectivity is poor it was possible to isolate pure monoacetal (19) in a yield of only 37% only after elaborate purification by crystallization twice (Helv. Chim. Acta 1981, 64 (7), 2471) This synthesis is also unsuitable for industrial implementation.

It is an object of the present invention to provide a process for preparing $C_{10}$-dialdehyde monoacetals which can be implemented on the industrial scale and has maximum flexibility in relation of the protective group.

We have found that this object is achieved by a process for preparing 2,7-dimethyl-2,4,6-octatrienal monoacetals of the general formula I,

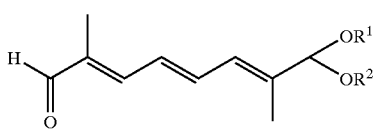

I in which the substituents $R^1$ and $R^2$ may, independently of one another, be $C_1$–$C_8$-alkyl or, together with the oxygen atoms and the carbon atoms to which they are bonded, form a 1,3-dioxolane or 1,3-dioxane ring of the following structures

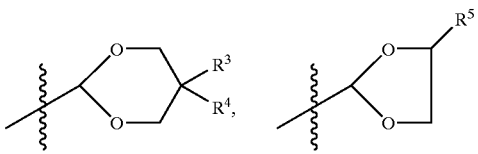

in which $R^3$ and $R^4$, and $R^5$ may each, independently of one another, be hydrogen or $C_1$–$C_4$-alkyl, which comprises a) condensing an ester phosphonium salt of the general formula II or an ester phosphonate of the general formula III,

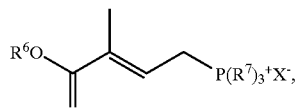

II

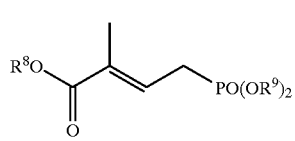

III in which the substituents have, independently of one another, the following meaning:

$R^6$ $C_1$–$C_8$-alkyl;

$R^7$ aryl;

$X^-$ an anion equivalent of an inorganic or organic acid;

$R^8$ and $R^9$ $C_1$–$C_8$-alkyl;

with an aldehyde of the formula IV

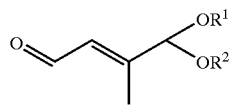

IV in a Wittig or Wittig-Horner reaction to give an acetal ester of the general formula V,

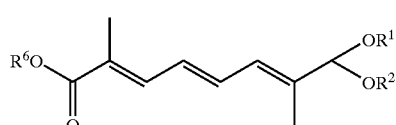

V in which the substituents $R^1$, $R^2$ and $R^6$ in the compounds IV and V have the abovementioned meaning, b) reducing the ester of the formula V to an acetal alcohol of the general formula VI,

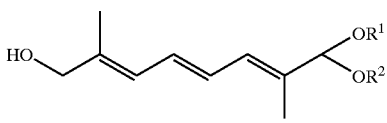

and c) oxidizing the alcohol to 2,7-dimethyl-2,4,6-octatrienal monoacetals of the general formula I.

It was surprisingly possible to achieve this object in a simple manner, starting from $C_5$ building blocks which have a fixed place in polyene synthesis and are easily obtainable on the industrial scale (cf. Carotenoids, Vol. 2, "Synthesis", pp. 115 ff.; Birkhauser Verlag 1996).

In the case of open-chain acetals, alkyl radicals which may be mentioned for $R^1$ and $R^2$ are linear or branched $C_1$–$C_8$-alkyl chains, e.g. methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl and n-octyl.

Preferred alkyl radicals for $R^1$ and $R^2$ are methyl, ethyl, n-propyl and 1-methylethyl, particularly preferably methyl and ethyl.

Alkyl radicals which may be mentioned for $R^3$ to $R^5$ are linear or branched $C_1$–$C_4$-alkyl chains, e.g. methyl, ethyl, n-propyl, 1-methylethyl, n-butyl, 1-methylpropyl, 2-methylpropyl and 1,1-dimethylethyl.

Preferred radicals for $R^3$ to $R^5$ are hydrogen and methyl.

Alkyl radicals which may be mentioned for $R^6$, $R^8$ and $R^9$ are linear or branched $C_1$–$C_8$-alkyl chains, e.g. methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl and n-octyl.

Preferred alkyl radicals for $R^6$, $R^8$ and $R^9$ are methyl, ethyl, n-propyl and 1-methylethyl, particularly preferably methyl and ethyl, very particularly preferably ethyl.

The term aryl for $R^7$ refers to conventional aryl radicals occurring in phosphines and phosphonium salts, such as phenyl, tolyl, naphthyl, optionally substituted in each case, preferably phenyl.

The radical $X^-$ represents one anion equivalent of an inorganic or organic acid, preferably a strong inorganic or organic acid.

The term strong acid encompasses hydrohalic acids (especially hydrochloric acid and hydrobromic acid), sulfuric acid, phosphoric acid, sulfonic acids and other inorganic or organic acids with a comparable degree of dissociation. Strong organic acids also mean in this connection $C_1$–$C_6$-alkanoic acids such as formic acid, acetic acid, propionic acid, butyric acid and caproic acid.

Particularly preferred anions which should be mentioned are acids selected from the group consisting of hydrochloric acid, hydrobromic acid, sulfuric acid, phosphoric acid, formic acid, acetic acid and sulfonic acids, very particularly preferred $Cl^-$, $Br^-$, $C_nH_{2n+1}$—$SO_3^-$ (with n=1–4), Ph—$SO_3^-$, p—Tol—$SO_3^-$ or $CF_3$—$SO_3^-$.

The first step a) in the process of the invention comprises the olefination reaction of a $C_5$-ester phosphonium salt of the general formula II or of a $C_5$-ester phosphonate of the general formula III with a $C_5$-acetal aldehyde of the general formula IV

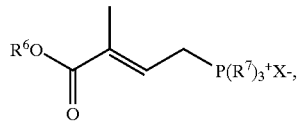

II

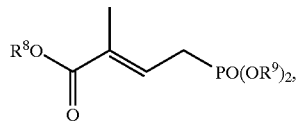

III

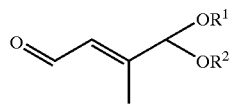

IV in which the substituents have the meaning mentioned at the outset.

A preferred embodiment of process step a) comprises using an ester phosphonate of the general formula III in which the substituents $R^8$ and $R^9$ are, independently of one another, $C_1$–$C_3$-alkyl, particularly preferably methyl or ethyl, very particularly preferably ethyl.

A likewise preferred embodiment of process step a) comprises using as aldehyde a compound of the formula IVa

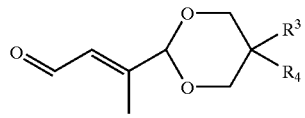

IVa in which the substituents $R^3$ and $R^4$ are, independently of one another, hydrogen and/or methyl, preferably in each case jointly hydrogen or methyl, particularly preferably jointly methyl.

The Wittig condensation of the phosphonium salt II with the aldehyde IV or the Wittig-Horner condensation of the phosphonate III with IV to give a $C_{10}$-acetal ester of the formula V is carried out under the conditions typical for these reactions (see Carotenoids, Vol. 2, "Synthesis", pp. 79 ff.; Birkhauser Verlag, 1996, and literature cited therein).

Condensation of II with IV can be carried out, for example, in an inert organic solvent, e.g. in open-chain or cyclic ethers such as diethyl ether, diisopropyl ether, methyl tert-butyl ether, 1,4-dioxane or THF, in halogenated hydrocarbons such as dichloromethane, chloroform, in aromatic hydrocarbons such as toluene, xylene or benzene, or in polar solvents such as dimethylformamide, dimethyl sulfoxide or acetonitrile. Preferred solvents are toluene, THF and DMSO or mixtures thereof.

It is possible to use as base all the bases customary for Wittig condensations, e.g. alkali metal hydroxides such as sodium hydroxide, potassium hydroxide or lithium hydroxide; alkali metal hydrides such as sodium hydride or potassium hydride.

Other suitable bases are organolithium compounds such as, for example, n-butyllithium, tert-butyllithium, phenyllithium or alkali metal amides such as lithium, potassium or sodium amide, lithium diisopropylamide or else alkali metal hexamethyldisilazides. The base preferably employed for the Wittig reaction of the invention is sodium or potassium hexamethyldisilazide, or potassium or sodium amide.

The amount of base employed is usually in the range from 0.8 to 5 mol, preferably 1 to 3 mol, per mole of the phosphonium salt II employed.

If X⁻ is a halide anion, it is also possible and advantageous to employ oxiranes as latent bases (see Chem. Ber. 1974, 107, 2050).

The bases preferably used for this Wittig reaction are solutions of alkali metal alcoholates in the corresponding alcohol or oxiranes, especially 1,2-epoxybutane, without additional solvent or in a mixture with one of the abovementioned solvents or a lower alkanol.

The conditions used for the Wittig-Horner reaction of III with IV are likewise those typical for this reaction.

In this case too, one of the abovementioned inert organic solvents is used, and a solution of an alkali metal alcoholate in the corresponding alkanol is preferably employed as base. However, in the case of the Wittig-Horner reaction, it is also possible to use the bases additionally mentioned above for the Wittig reaction with the exception of the oxiranes.

In the next steps of the process, the ester V is converted into the corresponding aldehyde.

Various methods are described in the literature for converting esters directly into aldehydes. However, these methods involve complex hydrides which are not available industrially, such as, for example, piperazinylaluminum hydrides (Chem. Lett. 1975, 215) or reagents which are difficult to handle industrially, such as, for example, diisobutylaluminum hydride, which additionally requires low reaction temperatures (–70° C.).

However, an industrial process must comply with the following requirements:

the reaction must take place completely and with maximal selectivity in order to avoid elaborate and costly separation operations extreme reaction conditions, especially low temperatures, must be avoided the reagent must be available industrially in relatively large quantities and be easy to handle from the viewpoint of safety.

On the basis of these requirements, the ester group is converted in the process of the invention in a two-stage procedure [stages b) and c)] into the aldehyde function.

In step b), the ester of the formula V is initially reduced to the corresponding alcohol of the formula VI.

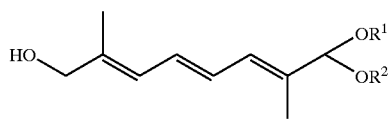

VI

It is possible in principle to employ for this step all hydride reagents described for reducing esters to alcohols, for example alkali metal borohydrides or alkali metal aluminum hydrides.

A preferred embodiment of process step b) comprises carrying out the reduction of the ester function with a sodium aluminum hydride compound, particularly preferably with sodium dihydrobis(2-methoxyethoxy)aluminate.

In accordance with the abovementioned requirements for an industrial process, the commercially available concentrated toluene solution of sodium dihydridobis(2-methoxyethoxy)aluminate ("Vitride®") is particularly advantageous. This reagent is not pyrophoric, not sensitive to oxygen (GIT Fachz. Lab. 9/96, 914) and, as a liquid, is considerably easier to handle in an industrial process than are solid complex hydrides such as, for example, lithium aluminum hydride.

The reaction is preferably carried out in such a way that the ester of the formula V is introduced into a solvent which is inert toward hydride reagents, such as, for example, toluene, open-chain or cyclic ethers, glycol ethers or a mixture of the solvents, and the reducing agent is metered in at a temperature in the range from –20° C. to 30° C., preferably from –10° C. to 10° C., particularly preferably from –5° C. to 0° C.

It is usual to employ at least 2 equivalents of hydride per equivalent of ester, i.e. at least 0.5 mol of lithium aluminum hydride/mol of ester or 1.0 mol of Vitride/mol of ester. However, in order to achieve complete conversion, it is advantageous to employ a certain excess of reducing agent. This excess is in the range from 10 to 50 mol %, preferably 20 to 30 mol %.

In the preferred embodiment of the process of the invention, the $C_{10}$-acetal ester V is reduced with the toluene solution of Vitride to the $C_{10}$-acetal alcohol VI. An aqueous workup results in a virtually quantitative yield of a crude product which can be employed directly, without purification, in the next stage c).

Oxidation of a $C_{10}$-acetal alcohol of the formula VIa to the corresponding aldehyde has not to date been described in the literature.

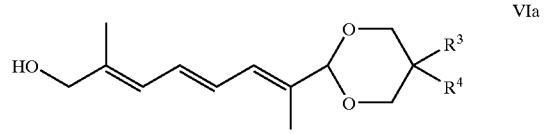

VIa

The closest prior art is the oxidation of a $C_{10}$-dimethyl acetal alcohol VII to the corresponding aldehyde.

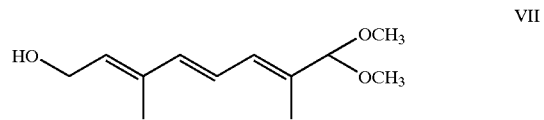

VII

As described in Helv. Chim. Acta 1966, 49, 369, this reaction is carried out with a large excess of manganese dioxide in a reaction time of 60 hours. The disadvantage of this process is, apart from the extremely long reaction time and the small yield, the use of a multimolar excess of oxidizing agent together with a not inconsiderable complexity in the removal of solids and the disposal of the manganese salts.

The oxidation processes mentioned in DE-A-3705785, DE-A-4440286, DE-A-4440287 and EP-A-0 718 283 for converting polyene alcohols into polyene aldehydes are suitable, inter alia, for the oxidation of VI to I in step c) of the process of the invention. However, catalytic methods will be preferred from the abovementioned economic, ecological and technical viewpoints of the process. Catalysts which can be employed for this purpose are, inter alia, ruthenium compounds such as tetrapropylammonium perruthenate, tris(triphenylphosphine)ruthenium(II) chloride or 1,5-cyclooctadieneruthenium(II) chloride in amounts of from 2 to 4 mol % in the presence of at least stoichiometric amounts of 4-methylmorpholine N-oxide as cooxidant (see J. Chem. Soc. Chem. Commun. 1987, 1625).

Catalytic oxidation of VI to I preferably takes place with a mixture comprising 2,2,6,6-tetramethylpiperidin-1-oxyl/copper(I) chloride/dimethylformamide/oxygen or with a mixture comprising 4-hydroxy-2,2,6,6-tetramethylpiperidin-1-oxyl/copper(I) chloride/dimethylformamide/oxygen in dimethylformamide as solvent. Further details of the oxidation are to be found, inter alia, in DE-A-3705785 and EP-A-0 718 283.

DE-A-3705785 and EP-A-0 718 283 describe oxidations of allyl alcohols which are substituted by methyl in the position β to the alcohol group, that is to say display no steric hindrance. It was therefore unexpected and surprising that the application of this reaction to allyl alcohols of the formula VI with methyl substituents in the a position provides, in complete and smooth conversion, the corresponding α,β-unsaturated aldehyde.

The process of the invention achieves the object described at the outset by a process which a) starts from precursors which are easily obtainable industrially, b) leads to the desired product in high overall yield in an only three-stage synthesis with simple process steps without c) the need to purify intermediates by elaborate process steps.

The invention also relates to acetal esters of the general formula Va

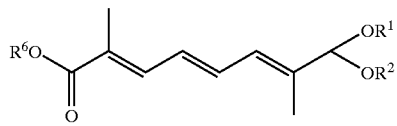

Va in which the substituents have, independently of one another, the following meaning:

$R^6$ $C_1-C_8$-alkyl;

$R^1$ and $R^2$ $C_1-C_8$-alkyl or together with the oxygen atoms and the carbon atoms to which they are bonded a 1,3-dioxolane or 1,3-dioxane ring of the following structures,

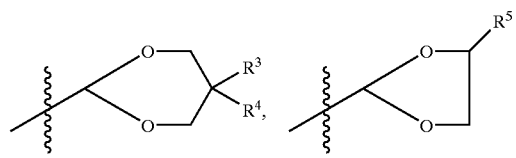

in which $R^3$ and $R^4$, and $R^5$ may each, independently of one another, be hydrogen or $C_1-C_4$-alkyl, where $R^1$ and $R^2$ are not methyl when $R^6$ is methyl.

Preferred acetal esters have the formula Vb

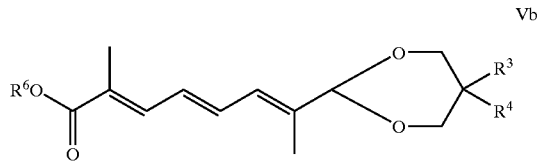

Vb in which $R^6$ is $C_1-C_4$-alkyl, and the substituents $R^3$ and $R^4$ may jointly be either hydrogen or methyl.

The invention additionally relates to acetal alcohols of the general formula VI

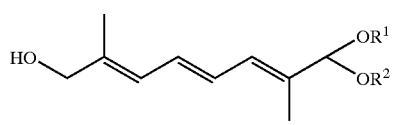

VI in which the substituents have, independently of one another, the following meaning:

$R^1$ and $R^2$ $C_1-C_8$-alkyl or together with the oxygen atoms and the carbon atoms to which they are bonded a 1,3-dioxolane or 1,3-dioxane ring of the following structures,

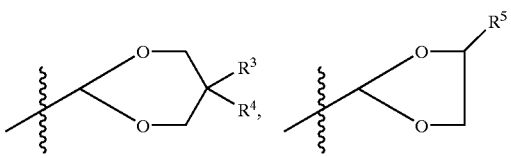

in which $R^3$ and $R^4$, and $R^5$ may each, independently of one another, be hydrogen or $C_1-C_4$-alkyl.

Preferred acetal alcohols have the formula VIa

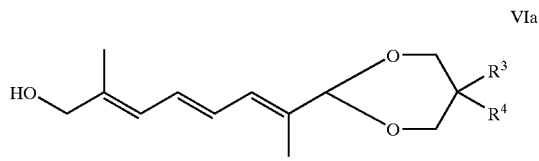

VIa in which the substituents $R^3$ and $R^4$ may jointly be either hydrogen or methyl.

Concerning the definition of the substituents $R^1$ to $R^6$—in the general and preferred embodiment—reference may be made to the explanations given at the outset.

The process of the invention is to be illustrated in detail by the following example.

EXAMPLE a) Preparation of the $C_{10}$-acetal Ester (Vc)

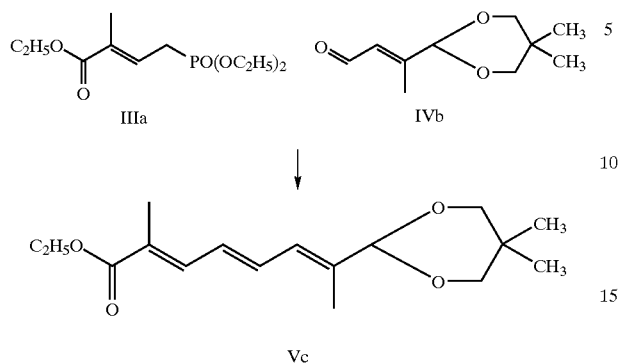

145 g (0.55 mol) of $C_5$-ester phosphonate IIIa and 103 g (0.55 mol) of $C_5$-acetal aldehyde IVb were introduced into 1250 ml of methylene chloride. At 0° C., a solution of 43 g (0.60 mol) of Na ethoxide in 163 g of ethanol was added over the course of 1 h. The mixture was stirred at 0° C. for 1 h and then at room temperature for 1 h. Firstly 60 g of 10% strength aqueous acetic acid and then 500 ml of semisaturated brine were added to the reaction mixture. The organic phase was separated off, washed twice with a mixture of 250 ml of semisaturated brine and 50 ml of 10% strength aqueous acetic acid each time and once with 250 ml of water, dried over sodium sulfate and concentrated in a rotary evaporator. The oily residue was dried in vacuo under 1 mbar at 50° C. 163 g of the crude $C_{10}$-acetal ester Vc was obtained in quantitative yield. The crude product was employed directly in the next stage (reduction to the alcohol).

b) Preparation of the $C_{10}$-acetal alcohol VIc

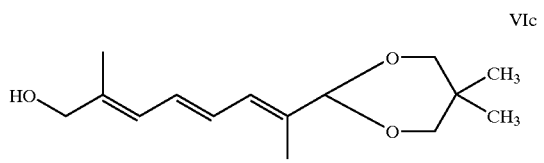

369 g of crude $C_{10}$-acetal ester Vc (prepared as in Example a) were dissolved in a mixture of 1000 ml of toluene and 1000 ml of tetrahydrofuran. While cooling to 0° C. to −2° C., 400 ml of a 70% strength toluene solution of sodium dihydridobis(2-methoxy-ethoxy)aluminate solution were added dropwise over the course of 1 h. The mixture was stirred at 0° C. for 2.5 h. Then, at 0° C., firstly 600 ml of an ethanol/hexane mixture (v/v, 40:60) and subsequently 300 ml of 15% strength aqueous sodium hydroxide solution and 1200 ml of n-hexane were added dropwise. Two clear phases were obtained. The aqueous phase was separated off and back-extracted once with 300 ml of toluene. The toluene extract was combined with the organic phase. The combined organic phases were washed several times with 400 ml of saturated brine each time until the aqueous phase had a pH of 9, dried over sodium sulfate and concentrated in a rotary evaporator. The oily residue was dried in vacuo under 1 mbar at 50° C. 315 g of the crude $C_{10}$-acetal alcohol VIc were obtained in quantitative yield. The crude product was employed directly in the next stage (oxidation to the aldehyde).

c) Preparation of the $C_{10}$-monoacetal aldehyde Ia

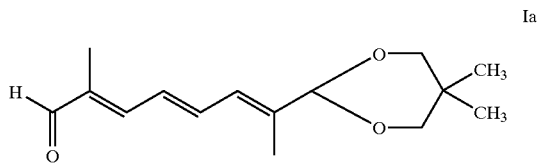

178 g of crude $C_{10}$-acetal alcohol VIc (prepared as in Example b) were introduced into 750 ml of dimethylformamide. After addition of 4.76 g of 2,2,6,6-tetramethylpiperidin-N-oxyl and 3.1 g of copper(I) chloride, oxygen gas was passed in through a gas-introduction stirrer at a temperature of 25° C. to 30° C. until a GC showed that reaction was complete. Oxygen present in the solution was driven out by brief introduction of nitrogen.

For workup, the mixture was mixed with 1000 ml of methyl tert-butyl ether and 1000 ml of semisaturated aqueous brine. The aqueous phase was separated off and back-extracted twice with 500 ml of a mixture of methyl tert-butyl ether and n-hexane (v/v, 1:1) each time. The organic phases were combined, washed three times with 300 ml of semisaturated aqueous brine each time, dried over sodium sulfate and concentrated in a rotary evaporator. The residue was dried in vacuo under 1 mbar at 50° C.

A total of 332 g of crude $C_{10}$-monoacetal aldehyde Ia was obtained as residue on evaporation from two identical batches.

This crude $C_{10}$-acetal aldehyde was dissolved at 60° C. in 2000 ml of a 1:1 diisopropyl ether/n-hexane mixture and filtered hot through silica gel as filtration aid. The filtrate was slowly cooled and stirred in an ice-water bath for several hours. The crystals were filtered off through a glass suction funnel, washed with a cold 1:1 diisopropyl ether/hexane mixture and dried in a stream of $N_2$. The first batch of crystals weighed 145 g (53% of theory) and had a melting point of 84.5 to 85° C. and a GC purity of 98.2%.

The mother liquor and wash liquors were evaporated. The residue was dissolved in a hot mixture of 300 ml of diisopropyl ether and 900 ml of n-hexane. The solution was slowly cooled and stirred at 0° C. overnight. The crystals were isolated as described above. The weight of the second batch of crystals was 23 g (8.4% of theory); GC purity: 97.7%).

The residue on evaporation of the mother liquor from the second batch of crystals was purified by flash chromatography on silica gel (eluent: cyclohexane/ethyl acetate 2:1). The purified $C_{10}$-monoacetal aldehyde was crystallized from diisopropyl ether/n-hexane 1:3 as described above. Weight of third batch of crystals: 46 g (16.7% of theory).

Total weight: 214 g of pure $C_{10}$-monoacetal aldehyde Ia crystals (77.8% of theory)

We claim:

1. A process for preparing 2,7-dimethyl-2,4,6-octatrienal monoacetals of the general formula I,

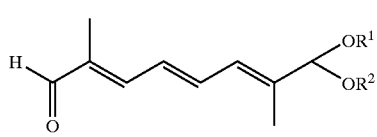

in which the substituents $R^1$ and $R^2$ may, independently of one another, be $C_1$–$C_8$-alkyl or, together with the oxygen atoms and the carbon atoms to which they are bonded, form a 1,3-dioxolane or 1,3-dioxane ring of the following structures

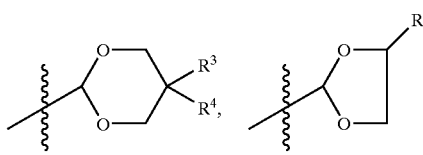

in which $R^3$ and $R^4$, and $R^5$ may each, independently of one another, be hydrogen or $C_1$–$C_4$-alkyl, which comprises a) condensing an ester phosphonium salt of the general formula II or an ester phosphonate of the general formula III,

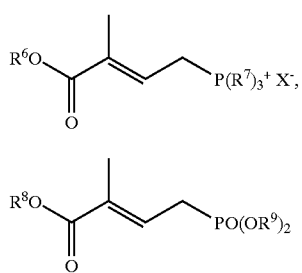

in which the substituents have, independently of one another, the following meaning:

$R^6$ $C_1$–$C_8$-alkyl;

$R^7$ aryl;

$X^-$ an anion equivalent of an inorganic or organic acid;

$R^8$ and $R^9$ $C_1$–$C_8$-alkyl;

with an aldehyde of the formula IV

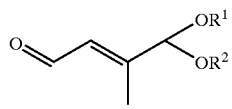

in a Wittig or Wittig-Horner reaction to give an acetal ester of the general formula V,

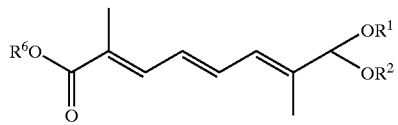

in which the substituents $R^1$, $R^2$ and $R^6$ in the compounds IV and V have the abovementioned meaning, b) reducing the ester of the formula V to an acetal alcohol of the general formula VI,

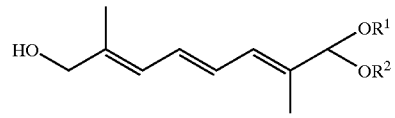

and c) oxidizing the alcohol to 2,7-dimethyl-2,4,6-octatrienal monoacetals of the general formula I.

2. A process as claimed in claim 1, wherein an ester phosphonate of the general formula III in which the substituents $R^8$ and $R^9$ are, independently of one another, $C_1$–$C_3$-alkyl is used in process step a).

3. A process as claimed in claim 1, wherein an aldehyde of the formula IVa

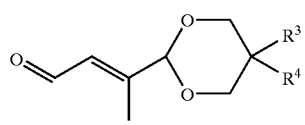

in which the substituents $R^3$ and $R^4$ may jointly be either hydrogen or methyl is used in process step a).

4. A process as claimed in claim 1, wherein the ester function is reduced in process step b) with a sodium aluminum hydride compound.

5. A process as claimed in claim 4, wherein the ester function is reduced in process step b) with sodium dihydrobis(2-methoxyethoxy)aluminate.

6. A process as claimed in claim 1, wherein the alcohol VI is oxidized to the corresponding aldehyde I in process step c) with a mixture comprising 2,2,6,6-tetramethylpiperidin-1-oxyl/copper(I) chloride/dimethylformamide/oxygen or with a mixture comprising 4-hydroxy-2,2,6,6-tetramethylpiperidine-1-oxyl/copper(I) chloride/dimethylformamide/oxygen.

7. An acetal ester of the formula Va

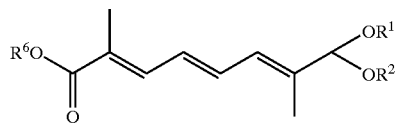

in which the substituents have, independently of one another, the following meaning $R^6$ $C_1$–$C_8$-alkyl;

$R^1$ and $R^2$ together with the oxygen atoms and the carbon atoms to which they are bonded a 1,3-dioxolane or 1,3-dioxane ring of the following structures,

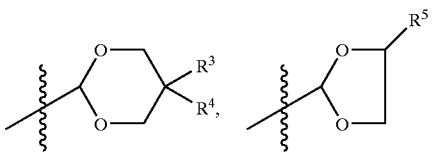

in which $R^3$ and $R^4$, and $R^5$ may each, independently of one another, be hydrogen or $C_1$–$C_4$-alkyl.

8. An acetal ester as claimed in claim 7, of the formula Vb

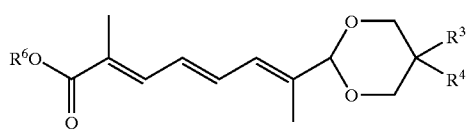

in which $R^6$ is $C_1$–$C_4$-alkyl, and the substituents $R^3$ and $R^4$ may jointly be either hydrogen or methyl.

9. An acetal alcohol of the formula VI

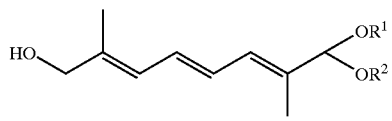

in which the substituents have, independently of one another, the following meaning:

$R^1$ and $R^2$ $C_1$–$C_8$-alkyl or together with the oxygen atoms and the carbon atoms to which they are bonded a 1,3-dioxolane or 1,3-dioxane ring of the following structures,

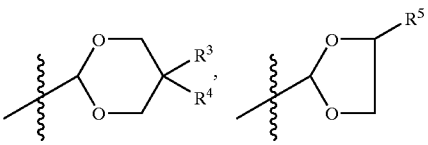

in which $R^3$ and $R^4$, and $R^5$ may each, independently of one another, be hydrogen or $C_1$–$C_4$-alkyl.

10. An acetal alcohol as claimed in claim 9, of the formula VIa

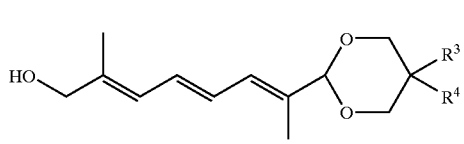

in which the substituents $R^3$ and $R^4$ may jointly be either hydrogen or methyl.

* * * * *